United States Patent [19]

Friese

[11] 4,312,348
[45] Jan. 26, 1982

[54] TAMPON PACK WITH A LUBRICANT DEPOT IN THE PACKAGING

[75] Inventor: Axel Friese, Wuppertal, Fed. Rep. of Germany

[73] Assignee: Dr. Carl Hahn, G.m.b.H., Dusseldorf, Fed. Rep. of Germany

[21] Appl. No.: 139,314

[22] Filed: Apr. 11, 1980

[30] Foreign Application Priority Data

Jul. 13, 1979 [DE] Fed. Rep. of Germany ....... 2928356

[51] Int. Cl.³ .................. A61F 15/00; A61F 13/20
[52] U.S. Cl. .................................. 128/263; 128/285
[58] Field of Search ..................... 128/263, 270, 285

[56] References Cited

U.S. PATENT DOCUMENTS 3,139,886  7/1964  Tallman et al. ............. 128/263
3,335,726  8/1967  Maranto ..................... 128/270
3,358,686 12/1967  Asaka ........................ 128/263

*Primary Examiner*—C. Fred Rosenbaum
*Attorney, Agent, or Firm*—Jason Lipow

[57] ABSTRACT

A combination tampon and packaging therefor is provided for which a lubrication may be applied to the tampon only immediately before use. The combination provides a separating sleeve slideably surrounding the periphery of the forward portion of the tampon and being spaced away from the forward portion of the tampon. A lubricant is deposited on that portion of the sleeve spaced away from the forward end of the tampon and a wrapper is provided enclosing both tampon and the sleeve. On removing the wrapper, the tampon may be slid forward relative to the sleeve and the lubricant automatically transferred to the tampon immediately prior to use.

9 Claims, 8 Drawing Figures

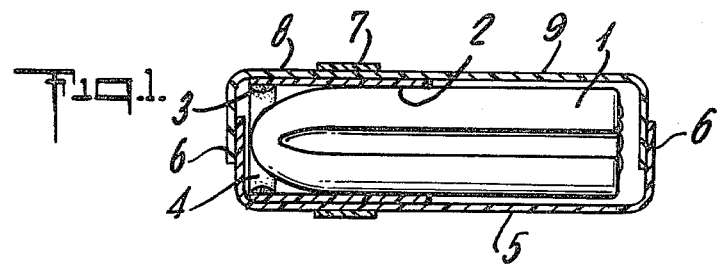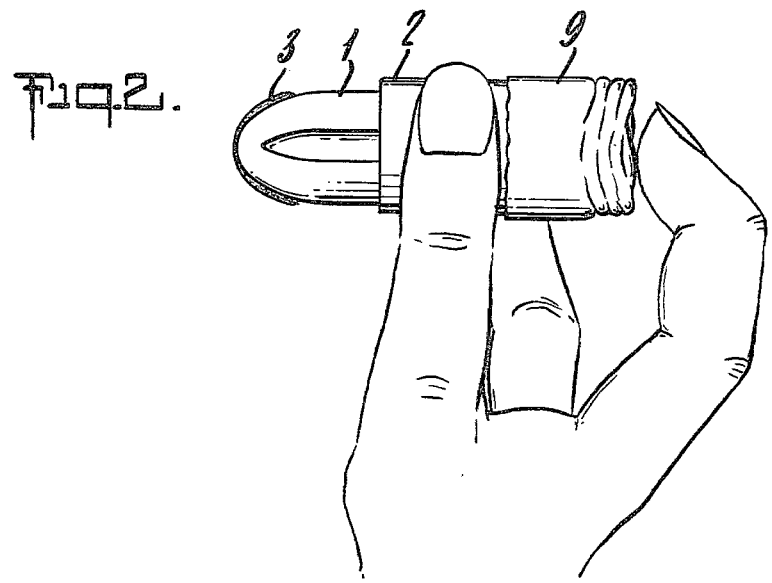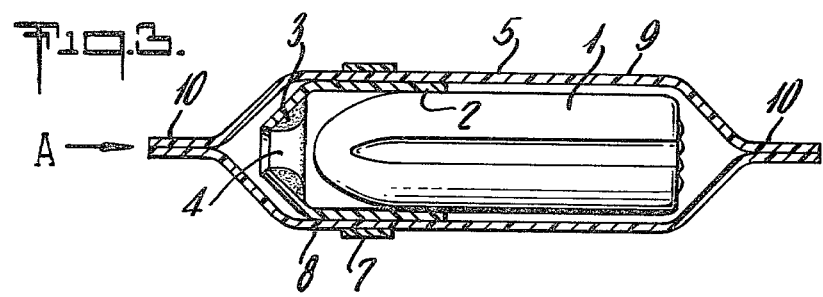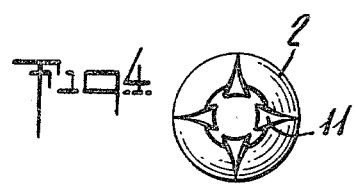

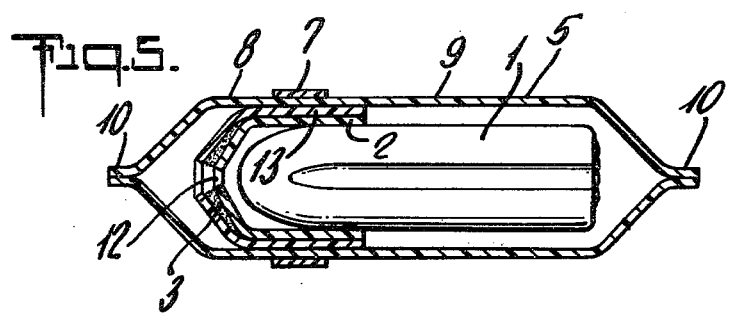
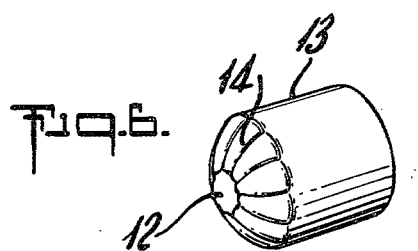
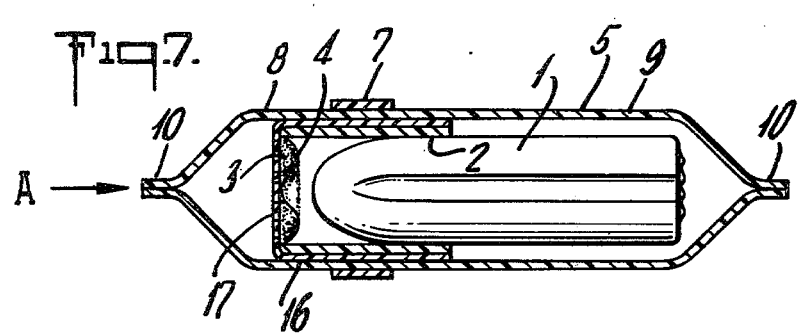
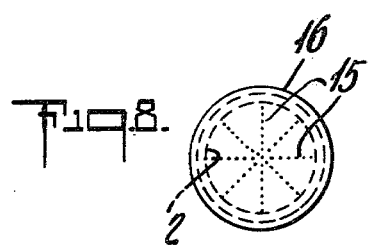

TAMPON PACK WITH A LUBRICANT DEPOT IN THE PACKAGING

BACKGROUND OF THE INVENTION

The invention relates to a tampon pack, in particular for female hygiene, wherein a depot for a substance is provided, which is transferred to the tampon when the latter is put into use.

The insertion of tampons frequently causes discomfort, in particular when the menstrual period is subsiding. Because insufficent moisture is then present, sliding of the tampon is impeded so that it is retained on the walls of the organ.

To overcome these difficulties, it has been proposed to coat the tampon, and in particular the rounded heads of the tampons, with a lubricant layer. However, tampons which have been coated in this way a long time before use can have the disadvantage that various lubricants are absorbed in the course of time by the highly absorbent tampon and the lubricating action is thus lost. On the other hand, tampons are known which have a solid lubricant substance which surrounds them and does not penetrate into the tampon, but this has the disadvantage that, since it has a closed surface, it strongly reduces the rate of absorption by the tampons. In the case of intermittent menstrual fluid flow, the time required for dissolving such a coating is insufficient under certain circumstances so that menstrual fluid flows past the unexpanded tampon.

SUMMARY OF THE INVENTION

It is the object of the invention to provide a tampon pack in which a lubricant is applied to the tampon, and in particular to its formed portion only, immediately before use so that the desired slipperiness is obtained. To achieve this object, a lubricant depot (i.e., a deposition of lubricant) is provided, according to the invention, in the packaging at a clear distance from the insertion or forward end of the tampon. When the pack is broken open or the tampon is pushed out of the pack, this lubricant is transferred automatically to the tampon.

The features of the tampon pack according to the invention can be seen from the patent claims.

A packaged tampon is known from U.S. Pat. No. 2,922,423, wherein a capsule with a medicament which is to be transferred to the tampon is provided in front of the insertion end of the tampon; compare column 5, lines 70 et seq. and FIG. 4. This printed publication does not, however, give any indication of a lubricant depot arranged separately from the tampon.

BRIEF DESCRIPTION OF THE DRAWINGS

In the following text, preferred embodiments of the tampon pack, according to the invention, with a lubricant depot are explained in reference to the drawings in which:

FIG. 1 shows a longitudinal section of a tampon pack having a cylindrical supporting sleeve as a transfer element, the lubricant depot being located on the inside of the forward end of the supporting sleeve in the zone of the rounded head of the tampon;

FIG. 2 shows the tampon of FIG. 1 in a position, in which half of it has been pushed out, after the pack has been broken open;

FIG. 3 shows a longitudinal section of a tampon pack similar to that in FIG. 1, the front end of the supporting sleeve being deformed conically;

FIG. 4 shows a front view of the tampon pack of FIG. 3, seen from the direction A;

FIG. 5 shows a longitudinal section of a tampon pack similar to that in FIG. 3, an additional cover being provided on the lubricant depot;

FIG. 6 shows an embodiment of a cover for the tampon of FIG. 5;

FIG. 7 shows a longitudinal section of a tampon pack which has a cylindrical supporting sleeve and in which the lubricant depot is located on a film to be pierced; and FIG. 8 shows a front view of the tampon of FIG. 7 seen in the direction A.

DETAILED DESCRIPTION OF THE INVENTION

According to FIG. 1, a supporting sleeve 2 is provided which surrounds the forward longitudinal section of the tampon 1. The supporting sleeve 2 can consist, for example, of sealable plastic films, paper, regenerated cellulose or an extruded tube. Preferably, the length of the supporting sleeve 2 corresponds to about one quarter up to one half of the length of the tampon 1. A lubricant depot 3 is provided on the inside of the front end of the supporting sleeve 2 spaced away from the insertion of forward end of the tampon 1. Preferably, the lubricant depot is distributed as an annular bead 4 around the periphery of the supporting sleeve 2. The height of the bead is such that transfer of the lubricant to the desired area in the conical zone of the insertion end of the tampon is ensured. Preferably, the height of the bead is about 1 to 3 mm. Instead of an annular arrangement, the lubricant depot 3 can also be distributed, spaced apart, around the periphery of the front part of the supporting sleeve. A packaging wrapper 5 encloses the supporting sleeve 2 and the tampon 1. The ends of the packaging wrapper 5 are closed by an enveloping or overlapping fold 6. The packaging wrapper 5 preferably consists of regenerated cellulose or of sealable films, such as polyethylene film, polypropylene film or a laminated film. A tear strip 7 extending over the periphery of the sleeve is provided on the front part of the packaging wrapper 5. After tearing, the packaging wrapper splits into a small front part 8 and a larger rear part 9. After removing the tear strip 7, the front part 8 of the packaging wrapper 5 can be pulled off forward, whilst the rear part 9 of the packaging wrapper 5 is firmly joined to the supporting sleeve 2, preferably to the rear of the tearing end.

FIG. 2 shows the opened tampon pack of FIG. 1, about one half of the tampon already being pushed out of the supporting sleeve and the lubricant having been transferred to the insertion end of the tampon.

The tampon pack in FIG. 3 differs from the pack in FIG. 1 mainly in that the front zone of the supporting sleeve 2 tapers conically and the lubricant depot is located on the inside of this conical zone. The packaging wrapper 5 is closed by a partially sealed end 10. The conical zone of the supporting sleeve according to FIGS. 3 and 4 preferably has inward folds or slots 11, as shown in FIG. 4. The conical shape makes it possible to vary the position of the lubricant substance on the insertion end of the tampon 1. In this case also, an arrangement of the lubricant as an annular bead 4 is preferred. In this embodiment, it is advantageous to cover the inside of the conical zone containing the lubricant depot 3 with a cover 13 which has a central opening 12, as shown in FIG. 5. The cone angle of the conical zone of the supporting sleeve 2 is preferably smaller than the cone angle of the rounded head of the tampon so that, when the tampon 1 is pushed out, the lubricant is forced out in the direction of the opening of the conical zone.

In FIG. 6, an embodiment of a cover 13 is shown in the ready-for-use state. The cover has chamber-like cavities 14 which are embossed radially and serve to receive the lubricant.

The tampon pack according to FIG. 7 is distinguished in particular in that a membrane 16 is put over the front zone of the supporting sleeve 2. This membrane cover 16 is preferably sealed to the supporting sleeve 2. The membrane preferably consists of a plastic film or of paper. At least that part 17 of the membrane 16 which covers the front opening of the supporting sleeve 2 is weakened, for example by a perforation 15, so that this part 17 can readily be pierced when the tampon is pushed out. The lubricant depot 3 is located on the inside of the part 17, which is to be pierced, of the membrane cover 16. In this case also, the lubricant is preferably applied in the form of an annular bead 4, the area of application being selected in accordance with that zone of the tampon to which the lubricant is to be transferred. Preferably, the internal diameter of the bead 4 is up to 8 mm. The bead height and the bead width are such that an adequate amount of lubricant is transferred to the tampon 1.

The lubricants which can be used are all the conventional lubricants for tampons, as long as they impart an adequate slipperiness to the tampon. The consistency of the lubricants is such that lubricant does not prematurely run out of the depot even on prolonged storage at temperatures of 30° C. Examples of lubricants are soaps, gelatine, polyvinyl acetates, polyvinylpyrrolidones, polyglycols, pectinates, gums, dextrin, oleates, methylcellulose, glucosides, long-chain fatty acids and/or carboxymethylcellulose. If desired, these lubricants can contain additives, such as plasticizers, solvents, preservatives and the like.

What is claimed is:

1. In combination, a tampon for digital insertion and packaging therefor comprising:

said tampon having a forward end and a rear end;

a supporting sleeve having a forward end and a rear end, a rear portion of said supporting sleeve slidably surrounding the periphery of a forward portion of the tampon and the forward end of said sleeve spaced away from the forward end of the tampon;

a lubricant depot on the inside of said sleeve, at the forward portion thereof spaced away from said forward end of said tampon; and a wrapper enclosing the support sleeve and said tampon, said wrapper being divided into a forward portion and a rear portion by a peripheral tear zone and said rear portion being joined to said supporting sleeve;

whereby said tampon may be packaged and remain free of lubricant and, when said wrapper is removed, said tampon may be slid forward relative to said sleeve whereupon, said lubricant will be transferred to the front portion of said tampon.

2. The tampon pack of claim 1 wherein the forward portion of the tampon is conical and the forward portion of said supporting sleeve tapers conically and the lubricant depot is located on the inside of this conical portion.

3. The combination of claim 2 wherein the cone angle of the forward portion of the supporting sleeve is smaller than the cone angle of the forward portion of the tampon.

4. The tampon pack of claim 2 wherein a cover is provided between the lubricant depot and the forward end of the tampon, said cover provided with at least one opening for allowing said lubricant to transfer to said tampon and for expelling said tampon from said pack.

5. The combination of claim 4 wherein said cover is provided with a central opening and elongated radically spaced opening.

6. The combination of claim 1 wherein said supporting sleeve comprises a membrane overlying the forward end thereof, said membrane having weakened areas and having said lubricant depot on its inside surface whereby said tampon may be slid against said lubricant depot and thereby have said lubricant transferred thereon and further slid through said weakened areas.

7. The combination of claim 1 wherein the lubricant depot is formed as an anular bead.

8. The tampon pack of claim 1 wherein said wrapper is closed at the forward end by an overlying fold.

9. The combination of claim 1 wherein said wrapper is closed at the forward end by a partable seal.

* * * * *